United States Patent [19]

Saari

[11] 4,456,604
[45] Jun. 26, 1984

[54] 1-(3-HALO-2-PYRIDINYL) PIPERAZINE

[75] Inventor: Walfred S. Saari, Lansdale, Pa.

[73] Assignee: Merck & Co., Inc., Rahway, N.J.

[21] Appl. No.: 397,651

[22] Filed: Jul. 12, 1982

Related U.S. Application Data

[63] Continuation-in-part of Ser. No. 362,081, Mar. 29, 1982, abandoned, which is a continuation-in-part of Ser. No. 267,120, May 26, 1981, abandoned.

[51] Int. Cl.$^3$ .................. C07D 401/04; A61K 31/495
[52] U.S. Cl. ...................................... 424/250; 544/360
[58] Field of Search .......................... 544/360; 424/250

[56]  References Cited

U.S. PATENT DOCUMENTS

| | | | |
|---|---|---|---|
| 2,606,906 | 8/1952 | Hultquist et al. | 544/360 |
| 2,663,706 | 12/1953 | Conroy | 544/295 |
| 2,958,694 | 11/1960 | Jannsen | 544/360 |
| 3,177,219 | 4/1965 | Brossi et al. | 544/360 |
| 3,773,951 | 11/1973 | Rodriguez | 424/250 |
| 4,078,063 | 3/1978 | Lumma, Jr. et al. | 544/360 |
| 4,081,542 | 3/1978 | Lumma, Jr. et al. | 544/295 |
| 4,082,844 | 4/1978 | Lumma et al. | 424/250 |
| 4,310,521 | 1/1982 | Weich et al. | 424/244 |

OTHER PUBLICATIONS

Thunus et al., Ann. Pharm. Fran. 32, 569–574 (1974).

*Primary Examiner*—Donald G. Daus
*Assistant Examiner*—S. A. Gibson
*Attorney, Agent, or Firm*—William H. Nicholson; Mario A. Monaco

[57] ABSTRACT

1-(3-Halo-2-pyridinyl)piperazine and its acid addition salts are selective $\alpha_2$-adrenergic receptor antagonists and thereby useful as antidepressant agents and for treating sedation caused by antihypertensive therapy.

3 Claims, No Drawings

1-(3-HALO-2-PYRIDINYL) PIPERAZINE

BACKGROUND OF THE INVENTION

This is a continuation-in-part of application, Ser. No. 362,081 filed Mar. 29, 1982, which in turn is a continuation-in-part of application, Ser. No. 267,120, filed May 26, 1981 abandoned.

This invention is concerned with novel 1-(3-halo-2-pyridinyl)piperazines or pharmaceutically acceptable salts thereof which have antidepressant activity and the ability to counteract the sedative side effect of antihypertensive agents. It also relates to a process for preparing the novel compounds, pharmaceutical compositions comprising the novel compounds and to a method of treating depression or antihypertensive agent induced sedation with the novel compounds.

The piperazinyl group is particularly ubiquitous among compounds with useful pharmacological properties. Piperazinylpyrazines (U.S. Pat. Nos. 4,081,542 and 4,082,844), piperazinylquinoxalines (French patent publication No. 2,236,499) and 2-piperazinyl-5 (and/or 6)-substituted pyridines (U.S. Pat. No. 4,078,063) are known anorexigenic agents which are also said to have antidepressant activity by virtue of their pharmacological influence on serotonin levels.

Now, with the present invention there is provided 1-(3-halo-2-pyridinyl)piperazines which are antidepressant agents and have the ability to counteract the sedative effect of antihypertensive agents by virtue of their ability to selectively antagonize $\alpha_2$-adrenergic receptor sites.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

Combinations of norepinephrine reuptake blockers with selective $\alpha_2$-adrenergic receptor antagonists, their effects being at least additive, form another aspect of this invention.

In addition to $\alpha_1$-adrenergic receptors which mediate postsynaptic responses to the neurotransmitter, norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norepinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

Mianserin, a clinically effective antidepressant which has been reported to have minimal in vivo norepinephrine reuptake inhibiting properties, blocks $\alpha_2$-adrenergic receptors. However, mianserin fails to exhibit any important selectivity for $\alpha_1$- or $\alpha_2$-adrenergic receptors suggesting that mianserin, in vivo, blocks $\alpha_1$-receptors at about the same dose required to block $\alpha_2$-receptors (Clineschmidt et al., *Arch. Int. Pharmacodyn. Ther.*, 242, 59 (1979)).

The compounds of the present invention, being highly selective for the $\alpha_2$-adrenergic receptor, have definite therapeutic advantages over the more non-selective $\alpha_1$-, $\alpha_2$-antagonists. Since $\alpha_1$- (or post-synaptic) blockade opposes the increase in nor-adrenergic transmission initiated through $\alpha_2$-blockade, compounds that selectively antagonize $\alpha_2$-adrenergic receptors induce enhanced neurotransmission at nor-adrenergic synapses. In addition, molecules with reduced $\alpha_1$-receptor blocking properties, such as the compounds of the present invention, produce less orthostatic hypotension, an undesirable side-effect (Synder, *Pharmakopsychiat,* 13, 62 (1980)).

The limiting side effect of sedation produced by some antihypertensive agents is believed to be associated with stimulation of presynaptic $\alpha_2$-adrenergic receptors. However, the lowering of blood pressure by these antihypertensive agents is not related to these receptors, but rather to postsynaptic adrenergic receptors (Birch et al., *Br. J. Pharmacol.*, 68, 107P (1979)). Selective $\alpha_2$-receptor antagonists should be useful in reducing the adverse effect of sedation produced by some antihypertensive drugs. Thus, the selective $\alpha_2$-receptor blocker, yohimbine, antagonizes the sedation produced by clonidine (Drew et at., *Br. J. Pharmacol.*, 67, 133 (1979)) and the locomotor depressant effects of methyldopa in rats (Clineschmidt et al., *Arch. Int. Pharmacodyn. Ther.*, 244, 231 (1980)). In addition, yohimbine has been reported to reduce clonidine-induced sedation in man (Autret et al., *Eur. J. Clin. Pharmacol.*, 12, 319 (1977)).

The compounds of the present invention, being highly selective for the $\alpha_2$-adrenergic receptor, effectively reduce the sedative effects of antihypertensive agents without affecting the blood pressure lowering properties.

DETAILED DESCRIPTION OF THE INVENTION

This invention is concerned with 1-(3-halo-2-pyridinyl)piperazine or a pharmaceutically acceptable salt thereof, wherein halo is chloro, bromo or fluoro, especially fluoro.

The pharmaceutically acceptable salts coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The novel compounds of the present invention are prepared by reaction of 2-Y-3-halo-pyridines of formula I with a piperazine of formula II.

The reaction sequence is as follows:

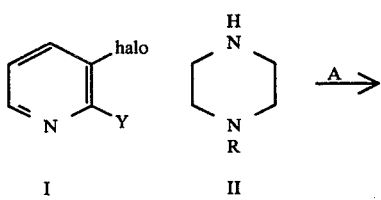

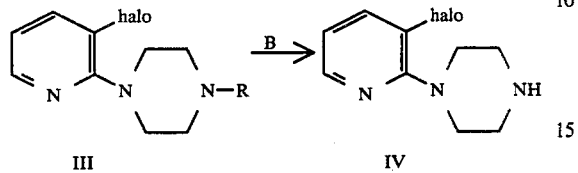

wherein

Y is halogen, especially chloro, $C_{1-5}$alkylsulfonyloxy, such as methanesulfonyloxy; or benzenoid arylsulfonyloxy such as, benzenesulfonyloxy or toluenesulfonyloxy; or $C_{1-5}$ alkylsulfonyl, such as methanesulfonyl; or benzenoid arylsulfonyl such as benzenesulfonyl or toluenesulfonyl and R is —H or

wherein $R^1$ is hydrogen, $C_{1-3}$ alkyl, benzenoid aryl such as phenyl, tolyl or xylyl, $C_{1-3}$ alkoxy, benzenoid aryloxy such as phenoxy, tolyloxy or xylyloxy, or —$NR^2R^3$ wherein $R^2$ and $R^3$ are independently hydrogen, or $C_{1-3}$ alkyl, or $R^2$ and $R^3$ taken together are tetramethylene, pentamethylene or —$(CH_2)_2O(CH_2)$—.

Process A takes place at temperatures ranging from about ambient to about 200° C., preferably under an inert atmosphere, e.g. $N_2$, He or Ar, until a substantial amount of desired compound of formula III is obtained, typically for a period of from about 0.25 to about 5 days, preferably from about 0.5 to about 3 days.

The reaction may be conducted neat, in the absence of solvent or in an inert organic solvent such as a $C_{2-5}$ alkanol, preferably butanol, acetonitrile, dimethylformamide, or dimethylsulfoxide.

For Process B, either acidic or basic hydolysis conditions may be used. For basic hydrolysis, an alkali metal hydroxide such as KOH or NaOH is preferred. At least 2 molar equivalents of base are necessary for best yields, but an excess of 2–10 equivalents is preferred. Solvents may be $H_2O$ or co-solvents miscible with $H_2O$ such as methanol ethanol, ethyleneglycol, or DMF, may be added. The hydrolysis takes place at temperatures ranging from about ambient to about 200° C., preferably under an inert atmosphere, e.g., $N_2$, He or Ar, typically from about 1 hour to about 2 days preferable from 3 hours to 1 day.

For acidic hydrolysis, dilute or concentrated aqueous mineral acids, such as HCl or HBr, or dilute or concentrated sulfuric acid is preferred. Miscible organic solvents such as ethanol, acetic acid or ethylene glycol may be added. Reaction temperatures range from ambient to about 150° and an inert atmosphere is preferred. Reaction times from 1 hour to 2 days are required and preferred are times of 3 hours to 1 day.

Another process comprises removal of an N-alkyl, alkenyl or aralkyl group from the piperazine nitrogen. These groups are removed by reaction with one equivalent of cyanogen bromide, a carboalkoxy halide, carbohaloalkoxy halide, carboalkenoxy halide, carboaryloxyhalide or a carboaryl alkoxy halide in a non-aqueous, aprotic solvent such as ether, chloroform, toluene or benzene at a temperature from about 0° C. to the reflux temperature of the solvent to give the compounds of structure V:

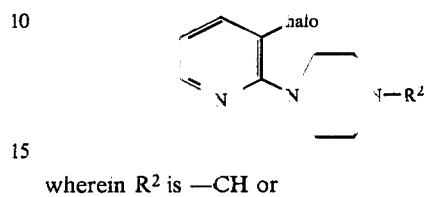

wherein $R^2$ is —CH or

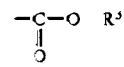

wherein $R^3$ is $C_{1-3}$ alkyl, halo-$C_{1-3}$ alkyl, $C_{2-4}$ alkenyl, such as vinyl or 1-propenyl, benzenoid aryl such as phenyl, or benzenoid aryl-$C_{1-3}$ alkyl such as phenyl-$C_{1-3}$ alkyl.

These groups, $R^2$, are then removed by acid or base hydrolysis as previously described for hydrolysis of the group

Some of the carbamates, V, are converted to the secondary amine by other routes. For example, the $\beta, \beta, \beta$-trichloroethyl carbamate

is converted to the secondary amine by heating with excess zinc dust in a $C_{1-3}$ alkanol or aqueous acetic acid.

An alkenyl carbamate

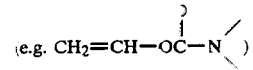

is removed by treating with anhydyrous HCl in a $C_{1-3}$ alkanol or HBr in acetic acid or $Hg(OAc)_2$ in aqueous acetic acid.

A preferred dealkylation procedure is to react a tertiary amine with phosgene, $COCl_2$, in a non-aqueous, aprotic solvent such as ether, $CHCl_3$ or toluene at about 0° to about 50° C. for 1–3 days followed by the addition of excess water with vigorous stirring at about 25° C. to about 100° C. for 1–12 hours.

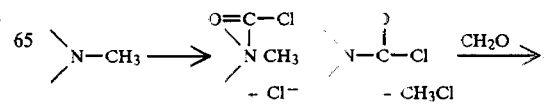

-continued

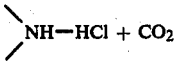

In the case of N-benzyl derivatives, the aralkyl group can be removed by all of the above procedures as well as by hydrogenation using Pd, Pt, PtO₂, or Raney Ni catalysts at about 1 atmosphere to about 50 atmospheres of pressure, at about 25°–100° C. for 3 hours to 1 day in a solvent such as an alcohol, acetic acid, or $H_2O$.

A further process is depicted as follows and comprises reduction of a pyridine-N-oxide:

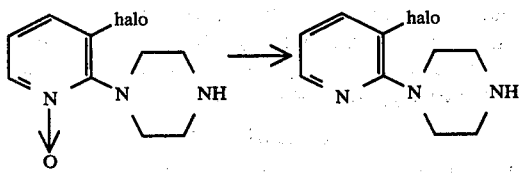

Suitable reducing agents are tin, zinc, iron, or sulfur dioxide in inorganic or organic acids; triphenylphosphine, sodium arsenite, ammonium sulfide, sodium dithionite, ferrous oxalate-granulated lead; and catalytic hydrogenation over palladium on carbon, Raney nickel and the like. Suitable solvents include polar solvents such as water, acetic acid, lower alcohols, and the like. The reduction is conducted at from about 0° to about 150° C.

An additional process comprises formation of the piperazine ring as follows:

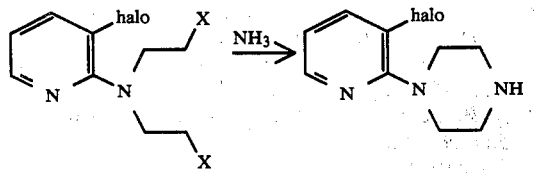

wherein the X groups are the same or different and X is a displaceable group such as halogen, tosyloxy, mesyloxy, or trialkylammonium. In general, the above process is effected by heating the reactants at from about 0° to about 250° C. in a polar solvent such as water, dimethylformamide, alcohols, and the like.

In the novel method of selectively antagonizing $\alpha_2$-adrenergic receptors in a patient, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

These doses are useful for treating depression or for treating sedation caused by antihypertensive chemotherapy.

If used in combination with a norepinephrine reuptake blocker anti-depressant, the dose of each is about half the recommended dose.

The compounds, or pharmaceutically acceptable salts thereof, of the present invention, in the described dosages, are administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples illustrate the present invention without, however, limiting the same thereto.

EXAMPLE 1

1-(3-Fluoro-2-Pyridinyl)Piperazine Dihydrochloride

A solution of 2-chloro-3-fluoropyridine (500 mg, 4.25 mmol) and anhydrous piperazine (3.66 g, 42.5 mmol) in 40 ml of n-butanol is stirred at reflux for 18 hours. After concentrating to dryness in vacuo, the residue is partitioned between toluene and dilute sodium hydroxide solution (5% w/v). The toluene layer is washed with a saturated sodium chloride solution, dried over $Na_2SO_4$, filtered and concenterated to 0.65 g of oil. Upon treatment of the oil with ethanolic hydrogen chloride and crystallization by dissolving the crude material in a minimum of methanol:ethanol (1:1) mixture and addition of ethyl acetate to incipient cloudiness, there is obtained 0.38 g., (35% yield) of product, m.p. 203°–210° C.

Calculated for $C_9H_{12}FN_3.2HCl$: C, 42.53; H, 5.55; N, 16.53. Found: C, 42.16; H, 5.64; N, 16.39.

Following the procedure substantially as described in Example 1, but substituting for the 2-chloro-3-fluoropyridine used therein, an equimolecular amount of 3-bromo-2-chloropyridine or 2,3-dichloropyridine there is produced respectively:

1-(3-bromo-2-pyridinyl)piperazine hydrochloride hemihydrate, m.p. 180° C. (dec.); and 1-(3-chloro-2-pyridinyl)piperazine hydrochloride m.p. 142°–144° C.

EXAMPLE 2

1-(3-fluoro-2-pyridinyl)piperazine dihydrochloride

Step A: Preparation of 1-(3-Fluoro-2-pyridinyl)-4-carbethoxy piperazine

A solution of 2-chloro-3-fluoropyridine (650 mg, 5.06 mmol) and ethyl N-piperazinocarboxylate (1.61 g, 10.2 mmol) in 60 ml of n-butanol is stirred at reflux under nitrogen for 18 hours. After concentrating to dryness under reduced pressure, the residue is dissolved in a mixture of ethyl acetate and water. The ethyl acetate extract is washed again with water, dried over anhydrous sodium sulfate, filtered and concentrated. The N-carbethoxy derivative of 1-(3-fluoro-2-pyridinyl)piperazine is further purified by chromatography over silica gel 60 (230–400 mesh).

Step B: Preparation of: 1-(3-Fluoro-2-pyridinyl)piperazine Dihydrochloride

A solution of 1-(3-fluoro-2-pyridinyl)-4-carbethoxy piperazine (700 mg, 2.76 mmol) in 50 ml of 6N hydrochloric acid is stirred at reflux under $N_2$ for 6 hours and then concentrated under reduced pressure. The residue is recrystallized from an ethanol-ethyl acetate mixture to give 1-(3-fluoro-2-pyridinyl) piperazine dihydrochloride.

EXAMPLE 3

1-(3-Fluoro-2-pyridinyl)piperazine hydrogen maleate

Step A: Preparation of: 1-(3-Fluoro-2-pyridinyl)-4-formylpiperazine

A solution of 2-chloro-3-fluoropyridine (500 mg, 4.25 mmol) and 1-piperazinecarboxaldehyde (970 mg, 8.50 mmol) in 40 ml of n-butanol is stirred at reflux for 18 hours under nitrogen. After concentrating to dryness in vacuo, the residue is partitioned between toluene and water. The toluene extract is washed with a saturated sodium chloride solution, dried over anhydrous sodium sulfate, filtered and concentrated to an oil. The N-formyl derivative is purified by chromatography over silica gel 60 (230-400 mesh).

Step B: Preparation of: 1-(3-Fluoro-2-pyridinyl)piperazine hydrogen maleate

A solution of 1-(3-fluoro-2-pyridinyl)-4-formylpiperazine (400 mg, 1.91 mmol) in 50 ml of ethanol containing 12 ml of 10% sodium hydroxide solution is stirred at reflux for 10 hours under nitrogen. After removing most of the ethanol under reduced pressure at 40°-45° C., organic products are extracted into toluene. The toluene extract is washed with a saturated sodium chloride solution, dried over anhydrous sodium sulfate, filtered and concentrated to an oil. This oil is dissolved in ethanol, treated with an equivalent of maleic acid, and the hydrogen maleate salt of 1-(3-fluoro-2-pyridinyl) piperazine is precipitated by the addition of ethyl acetate.

1-(3-Fluoro-2-pyridinyl)piperazine hydrogen maleate has m.p. 165°-166° C.

EXAMPLE 4

1-(3-Fluoro-2-pyridinyl)piperazine hydrogen maleate

Step A: Preparation of 1-Methyl-4-(3-fluoro-2-pyridinyl)piperazine

A solution of 2-chloro-3-fluoropyridine (1.0 g, 8.5 mmol) and N-methyl piperazine (4.26 g, 42.5 mmol) in n-butanol, 50 ml, is stirred at reflux for 18 hours. After concentrating under reduced pressure at 50° C., the residue is partitioned between ethyl ether and 50% NaOH solution. The ethyl ether extract is washed with a saturated sodium chloride solution, dried over $Na_2SO_4$, filtered and concentrated under reduced pressure. The oily product is converted to the hydrogen fumarate salt, mp 148°-149° C., by treatment with fumaric acid in methanol and precipitation with ethyl ether.

Step B: Preparation of 1-(3-Fluoro-2-pyridinyl)piperazine hydrogen maleate

To a solution of 1-methyl-4-(3-fluoro-2-pyridinyl)piperazine (0.98 g, 5.0 mmol) in toluene, 25 ml, cooled with an ice bath is added 3.96 g. of a 12.5% solution of phosgene in toluene. After stirring at 5°-10° C. for 1 hour, the mixture is allowed to warm to 20°-25° C. and remain at this temperature for 3 days. Water, 10 ml, is then added and the mixture stirred vigorously at 50° C. for 6 hours. The water layer is removed, made basic with 10% NaOH solution and the product extracted with ethyl acetate. The ethyl acetate extract is washed with a saturated NaCl-$H_2O$ solution, dried over anhydrous sodium sulfate, filtered and concentrated to an oil. This oil is dissolved in ethanol, treated with an equivalent of maleic acid, and the hydrogen maleate salt precipitated by the addition of ethyl acetate.

EXAMPLE 5

1-(3-Fluoro-2-Pyridinyl)piperazine dihydrochloride

Step A: Preparation of 1-Benzyl-4-(3-fluoro-2-pyridinyl)-piperazine dihydrochloride A solution of 2-chloro-3-fluoropyridine (1.0 g, 8.5 mmol) and N-benzylpiperazine (3.0 g, 17 mmol) in n-butanol, 50 ml, is stirred at reflux for 24 hours. After concentrating under reduced pressure at 50° C., the residue is partitioned between ethyl acetate and a 5% sodium hydroxide solution. The toluene layer is washed with a saturated sodium chloride solution, dried over anhydrous sodium sulfate, filtered and concentrated to an oil. Upon treatment of the oil with ethanolic hydrogen chloride and recrystallization from an ethanol-ethyl acetate mixture there is obtained the dihydrochloride of 1-benzyl-4-(3-fluoro-2-pyridinyl)piperazine.

Step B: Preparation of 1-(3-Fluoro-2-pyridinyl)piperazine dihydrochloride

A solution of 1-benzyl-4-(3-fluoro-2-pyridinyl)piperazine dihydrochloride (500 mg, 1.8 mmol) in glacial acetic acid, 20 ml, is shaken with 100 mg of a platinum oxide catalyst in an atmosphere of hydrogen at 50° C. and 2 atmospheres pressure until one equivalent of hydrogen has been taken up. The catalyst is removed by filtration and the filtrate concentrated under reduced pressure. The residue is recrystallized from an ethanol-ethyl acetate mixture to give the dihydrochloride of 1-(3-fluoro-2-pyridinyl)piperazine.

EXAMPLE 6

1-(3-Fluoro-2-pyridinyl)piperazine dihydrochloride

Step A: Preparation of 2-Chloro-3-fluoropyridine N-oxide

A mixture of 2-chloro-3-fluoropyridine (11.8 g, 0.10 mol) and 11.4 ml of 30% hydrogen peroxide in acetic acid, 70 ml, is stirred at 75° C. for 4 hours. Additional 30% hydrogen peroxide, three 5 ml portions, is added over 24 hours followed by 3 ml of a saturated sodium bisulfite solution. The reaction mixture is concentrated to approximately 25 ml under reduced pressure at 55°-60° C., diluted with water, 30 ml, and made basic with potassium carbonate. The crude N-oxide is extracted into ethyl acetate, dried over anhydrous magnesium sulfate, filtered and concentrated under reduced pressure. Chromatography over silica gel and elution with 2% MeOH-98% $CHCl_3$ (v/v) mixture gives 2-chloro-3-fluoropyridine N-oxide as a liquid.

Step B: Preparation of 2-(1-Piperazinyl)-3-fluoropyridine N-oxide

A solution of 2-chloro-3-fluoropyridine N-oxide (400 mg, 3.0 mmol) and piperazine (1.3 g, 15 mmol) in n-butanol, 15 ml, is stirred at reflux for 20 hours. After concentrating under reduced pressure at 55°-60° C., the residue is chromatographed over silica gel and the crude N-oxide eluted with a 50% methanol-methylene chloride solvent mixture. The appropriate eluate is concentrated to an oily residue of the title compound.

Step C: Preparation of 1-(3-fluoro-2-pyridinyl)piperazine dihydrochloride

A solution of 3-fluoro-2-piperazinylpyridine N-oxide (2 mmol) in 10 ml of glacial acetic acid is warmed to about 85° C. saturated with anhydrous hydrogen chloride gas and treated with a fine stream of sulfur dioxide for 1 hour. The acetic acid is removed under reduced pressure and the residue is crystallized from an ethanol-ethyl acetate mixture to give the title compound.

EXAMPLE 7

1-(3-fluoro-2-pyridinyl)piperazine hydrogen maleate

Step A: Preparation of 2-[N,N-Bis(2-hydroxyethyl)amino]-3-fluoropyridine

A solution of 2-chloro-3-fluoropyridine (1.0 g, 8.5 mmol) and diethanolamine (2.1 g, 20 mmol) in n-butanol, 50 ml, is stirred at reflux under nitrogen for 20 hours. After removing most of the n-butanol under reduced pressure at about 50° C., the residue is partitioned between ethyl acetate and 5% sodium hydroxide solution. The ethyl acetate layer is washed with a saturated solution of sodium chloride in water, dried over anhydrous sodium sulfate, filtered and concentrated. Chromatography of the residue over silica gel 60 (230–400 mesh) gives 2-[N,N-bis(2-hydroxyethylamino]-3-fluoropyridine.

Step B: Preparation of 2-[N-N-Bis(2-chloroethyl)amino]-3-fluoropyridine hydrochloride The diol product from Step A (800 mg, 4.0 mmol) is added to thionyl chloride, 10 ml, cooled to about 5° C, with an ice bath. The solution is allowed to warm to about 20° C. and then stirred at reflux for 6 hours. Unreacted thionyl chloride is removed under reduced pressure at about 45° C. Toluene, 10 ml, is added and then concentrated under reduced pressure at about 50° C. This process is repeated two more times to ensure complete removal of unreacted thionyl chloride from the residual dichloride hydrochloride.

Step C: Preparation of 1-(3-Fluoro-2-pyridinyl)piperazine hydrogen maleate

The crude dichloride hydrochloride residue from Step B is dissolved in absolute ethanol, 50 ml, saturated with anhydrous ammonia at about 20° C. and heated in a sealed vessel at about 100° C. for 20 hours. After concentrating under reduced pressure at about 40°–45° C., product is extracted into toluene. The toluene extract is washed with a saturated sodium chloride solution, dried over anhydrous sodium sulfate, filtered and concentrated to an oil. This oil is purified by chromatography over silica gel 60 (230–400 mesh) with elution by a 5% methanol-95% chloroform saturated with ammonia mixture and converted to the hydrogen maleate salt with an equivalent of maleic acid in ethanol-ethyl acetate.

EXAMPLE 8

Adrenergic Receptor Binding Assays for 1-(3-Halo-2-pyridinyl)piperazines and Related Compounds The $\alpha_1$- and $\alpha_2$-adrenergic receptor binding was determined for 1-(3-halo-2-pyridinyl)piperazines and a number of other structurally related compounds shown in Table I.

Extent of binding to the $\alpha_1$-adrenergic receptor was determined by the method of Greengrass and Bremner, *Eur. J. Pharmacol.*, 55, 323 (1979) and is expressed in Table I as Ki, representing the affinity of each compound for the [$^3$H] prazosin binding site in calf cerebral cortex.

Binding to the $\alpha_2$-adrenergic receptor was determined by the method of Lyon and Randall, *Life Sciences*, 26, 1121 (1980) and also is expressed in Table I as Ki representing the affinity of each compound for the [$^3$H] clonidine binding site in calf cerebral cortex.

TABLE I

Adrenergic Receptor Binding of 1-(3-Halo-2-pyridinyl)piperazine and Related Compounds

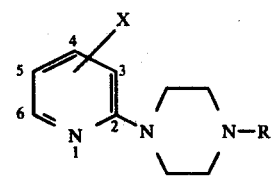

| | | | Adrenergic Binding Ki(nM) | | Ratio |
|---|---|---|---|---|---|
| Compound | X | R | $\alpha_2$ | $\alpha_1$ | $\alpha_1/\alpha_2$ |
| 1 | 3-F | H | 8.3 | 2300 | 277 |
| 2 | 3-Cl | H | 7.9 | 1800 | 228 |
| 3 | 3-Br | H | 11 | 1480 | 135 |
| 4 | 3-I | H | 42 | 1600 | 38 |
| 5[a] | 3-Br | —CH$_3$ | 2.9 | 160 | 55 |
| 6[b] | 6-Cl | H | 18 | 500 | 26 |
| 7[c] | H | H | 37 | 2400 | 65 |
| 8[b] | 5-Cl | H | 1000 | — | — |
| 9[d] | 6-Cl | H | 127 | 2400 | 19 |
| 10 | 3-Cl | H | 160 | 26000 | 163 |

[a] Ann. Pharm. franc. 32, 569 (1974).
[b] U.S. Pat. No. 4,078,063.
[c] U.S. Pat. No. 3,773,951
[d] U.S. Pat. No. 4,082,844

Of the compounds tested, the novel compounds of this invention (1, 2 and 3) clearly have the strongest affinity (lowest Ki), with the exception of compound 5, for the $\alpha_2$-adrenergic receptors, and the weakest affinity (highest Ki) for the $\alpha_1$-adrenergic receptors. Accordingly they have the greatest selectivity or ratio of Ki$_{\alpha 1}$/Ki$_{\alpha 2}$ as compared to any of the other tested compounds.

EXAMPLE 9

| Pharmaceutical Formulation | |
|---|---|
| Ingredient | Mg/Capsule |
| 1-(3-fluoro-2-pyridinyl)piperazine dihydrochloride | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 10

| Pharmaceutical Formulation - including a norepinephrine reuptake blocker | |
|---|---|
| Ingredients | Mg/capsule |
| 1-(3-fluoro-2-pyridinyl)pyrazine dihydrochloro | 3 |
| amitriptyline hydrochloride | 15 |
| starch | 75 |

| Pharmaceutical Formulation - including a norepinephrine reuptake blocker | |
|---|---|
| Ingredients | Mg/capsule |
| magnesium stearate | 7 |

The active ingredients, starch and magnesium stearate are blended together. The mixture is used to fill hard shell capsules of a suitable size at a fill weight of 100 mg per capsule.

EXAMPLE 11

| Pharmaceutical Formulation including an antihypertensive agent | |
|---|---|
| Ingredients | Mg/capsule |
| 1-(3-fluoro-2-pyridyl)pyrazine dihydrochloride | 6 |
| methyldopa | 250 |

| Pharmaceutical Formulation including an antihypertensive agent | |
|---|---|
| Ingredients | Mg/capsule |
| starch | 219 |
| magnesium stearate | 25 |

The active ingredient, starch and magnesium stearate are blended together. The mixture is used to fill hard shell capsules of a suitable size at a fill weight of 500 mg per capsule.

What is claimed is:

1. The compound 1-(3-fluoro-2-pyridinyl)piperazine or a pharmaceutically acceptable salt thereof.

2. An antidepressant pharmaceutical formulation comprising a pharmaceutical carrier and an effective antidepressant amount of 1-(3-fluoro-2-pyridinyl)piperazine or a pharmaceutically acceptable salt thereof.

3. A method of treating depression comprising the administration to a patient in need of such treatment of an effective antidepressant amount of 1-(3-fluoro-2-pyridinyl)piperazine or a pharmaceutically acceptable salt thereof.

* * * * *